(12) United States Patent
Ishida et al.

(10) Patent No.: US 10,751,046 B2
(45) Date of Patent: Aug. 25, 2020

(54) MEDICAL SUTURE NEEDLE

(71) Applicant: MANI, Inc., Utsunomiya-shi, Tochigi (JP)

(72) Inventors: Takashi Ishida, Utsunomiya (JP); Shinichi Akutsu, Utsunomiya (JP); Motoichi Sugino, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 141 days.

(21) Appl. No.: 16/068,130

(22) PCT Filed: Jan. 6, 2017

(86) PCT No.: PCT/JP2017/000304
§ 371 (c)(1),
(2) Date: Jul. 5, 2018

(87) PCT Pub. No.: WO2017/119495
PCT Pub. Date: Jul. 13, 2017

(65) Prior Publication Data
US 2019/0008513 A1 Jan. 10, 2019

(30) Foreign Application Priority Data
Jan. 6, 2016 (JP) .................... 2016-001002

(51) Int. Cl.
*A61B 17/06* (2006.01)
(52) U.S. Cl.
CPC ............ *A61B 17/06066* (2013.01); *A61B 2017/06014* (2013.01); *A61B 2017/06028* (2013.01); *A61B 2017/06071* (2013.01)
(58) Field of Classification Search
CPC .......... A61B 17/06066; A61B 17/3211; A61B 2017/06071; A61B 2017/0608;
(Continued)

(56) References Cited

U.S. PATENT DOCUMENTS

| 5,797,961 A | 8/1998 | Smith et al. |
| 7,655,024 B2* | 2/2010 | Cunningham ... A61B 17/06066 606/222 |
| 2011/0112575 A1* | 5/2011 | Tochimura ....... A61B 17/06066 606/222 |

FOREIGN PATENT DOCUMENTS

| JP | H09322898 A | 12/1997 |
| JP | 2004305397 A | 11/2004 |
| JP | 2009165638 A | 7/2009 |

OTHER PUBLICATIONS

International Search Report (ISR) for Application No. PCT/JP2017/000304 dated Apr. 4, 2017.
(Continued)

*Primary Examiner* — Diane D Yabut
*Assistant Examiner* — Majid Jamialahmadi
(74) *Attorney, Agent, or Firm* — Isshiki International Law Office; Joseph P. Farrar, Esq.

(57) ABSTRACT

A medical suture needle made of stainless steel includes a cutting blade component and a body part continuing to the cutting blade component. The cutting blade component, whose degree of thickness decreases from the body part to a sharp point, includes a first cutting blade part and a second cutting blade part continuing from the first cutting blade part. The first cutting blade part includes two first slanted surfaces formed sandwiching an apex and a first bottom surface sandwiched by the two first slanted surfaces. Cutting blades are formed at an edge constituting the apex and at edges where the first bottom surface and the two first slanted surfaces intersect. The second cutting blade part includes first slanted surfaces, second slanted surfaces having rims approximately parallel to the apex and formed on the respective first slanted surfaces, and a second bottom surface sandwiched by the second slanted surfaces.

2 Claims, 3 Drawing Sheets

(58) Field of Classification Search
CPC .. A61B 2017/0609; A61B 2017/06109; A61B 2017/06095; A61B 2017/32113; A61F 9/0133; C21D 9/26; D05B 85/00; A61M 5/32
USPC .................................. 606/222, 223; 112/222
See application file for complete search history.

(56) References Cited

OTHER PUBLICATIONS

Translation of the ISR for Application No. PCT/JP2017/000304 dated Apr. 4, 2017.
Written Opinion of the International Search Authority for Application No. PCT/JP2017/000304 dated Apr. 4, 2017.

* cited by examiner (a)

(b)

(c)

(d)

MEDICAL SUTURE NEEDLE

CROSS-REFERENCE TO RELATED APPLICATIONS

The present application is a national phase entry under 35 U.S.C. § 371 of International Application No. PCT/JP2017/000304, filed Jan. 6, 2017, which in turn claims priority from Japanese Patent Application No. 2016-001002 filed Jan. 6, 2016, the entire disclosures of which are hereby incorporated by reference herein.

TECHNICAL FIELD

The present invention relates to a medical suture needle used for suturing biotissue. It particularly relates to a medical suture needle having high strength and a small insertion mark.

BACKGROUND ART

Multiple kinds of medical suture needles having optimum shapes corresponding to the target suture sections are provided. Among them is a medical suture needle constituted by a sharp point and a cutting blade part continuing from the sharp point, wherein the cutting blade part has a triangular cross-section.

A medical suture needle described in Patent Document 1, for example, has a first cutting blade part, a second cutting blade part, and a third cutting blade part formed in a cutting blade component having a triangular cross-section. The first cutting blade part has side blades on either side of the peripheral surface formed as cutting blades, without a cutting blade formed on an apex. The second cutting blade part has a first recess part formed through parallel translation of slanted surfaces on either side of the peripheral surface toward the center of the triangular shape, thereby forming side blades on either side of the peripheral surface and forming a ridge blade on the apex. Furthermore, the third cutting blade part has side blades formed on either side of the peripheral surface and a ridge blade formed on the apex with each of the cutting blades that form the second cutting blade part keeping their respective angles.

Patent Document 1 discloses that large wall thickness and high bending strength can be obtained even when blade angles formed by the side blades and the ridge blade are made relatively small, and that the third cutting blade part can be formed continuing to the needle tip in a sharp state even when blade angles formed by the side blades and the ridge blade is made relatively small due to a second recess part, thereby providing high insertion property.

Moreover, reduction of resistance (improvement of insertion property) when passing the medical surgical needle through tissue, so as to reduce fatigue of the doctor when performing a suture operation is desired. In response to such desire, a medical suture needle called a cobra head shape where the size of the cutting blade part is larger than degree of thickness of the body part is provided.

PRIOR ART DOCUMENTS

Patent Documents

[Patent Document 1] JP 2009-165638A (U.S. Pat. No. 4,576,589)

DISCLOSURE OF INVENTION

Problem to be Solved by the Invention

The technology disclosed in Patent Document 1 may provide a high insertion property for the third cutting blade part made by two side blades and a ridge blade having sharp blade angles (20 to 30 degrees) since the second recess part is constituted by a slanted surface constituting a side blade and a slanted surface constituting the ridge blade. However, there is fear that wall thickness of the triangular central portion at the front end part of the third cutting blade part may be very thin, thereby decreasing the strength.

Furthermore, there is fear that the cobra head-shaped medical suture needle having the cutting blade part larger in width than degree of thickness of the body part may make a large incision, resulting in a large incision mark.

An object of the present invention is to provide a medical suture needle having a strength-improved front end part where a sharp point is formed and reducing insertion resistance while making the insertion mark smaller after passing through tissue.

Solution to the Problem

A medical suture needle according to the present invention for resolving the above problem is characterized by being made of stainless steel, including: a cutting blade component; and a body part continuing to the cutting blade component. The cutting blade component having a sharp point and formed with shape whose degree of thickness decreases from the body part to the sharp point includes: a first cutting blade part continuing from the sharp point; and a second cutting blade part continuing from the first cutting blade part. The first cutting blade part includes: two first slanted surfaces formed sandwiching an apex, and a first bottom surface sandwiched by the two first slanted surfaces. Cutting blades are formed at an edge constituting the apex and at edges where the first bottom surface and the two first slanted surfaces intersect. The second cutting blade part includes: the two first slanted surfaces formed sandwiching the apex; second slanted surfaces having rims, which are approximately parallel to the apex, formed on the two respective first slanted surfaces, or on the apex side of the second slanted surfaces, wherein an angle made by sandwiching the apex by the second slanted surfaces is smaller than the angle made sandwiching the apex by the first slanted surfaces; and a second bottom surface sandwiched by the second slanted surfaces, wherein cutting blades are formed at an edge constituting the apex and at edges where the second bottom surface and the two second slanted surfaces intersect.

With the above medical suture needle, a third cutting blade part continuing to the second cutting blade part and the body part is formed on the cutting blade component. The third cutting blade part includes: two first slanted surfaces formed sandwiching the apex; grooves comprising slanted surfaces having a pair of an upper rim and a lower rim approximately parallel to the apex and respectively formed on the two first slanted surfaces. An angle made by sandwiching the apex by the slanted surfaces is smaller than the angle made by the first slanted surfaces. Third slanted surfaces formed in each of the grooves on the side separated from the apex; and a third bottom surface sandwiched by the third slanted surfaces, wherein cutting blades are formed at an edge constituting the apex and at edges where the third bottom surface and the two third slanted surfaces intersect.

Advantageous Effect of the Invention

The medical suture needle (referred to as 'suture needle' hereafter) according to the present invention includes a cutting blade component that includes a first cutting blade part having a sharp point and formed with a shape whose degree of thickness decreases from the body part to the point (tapered shape), and a second cutting blade part continuing from the first cutting blade part. The first cutting blade part has a triangular cross-section due to the two first slanted surfaces sandwiching the apex, and the first bottom surface sandwiched by the two first slanted surfaces. As a result, the first cutting blade part continuing from the point has a sufficient thickness, and thus has a high bending strength.

Moreover, the first cutting blade part has cutting blades formed at the edge constituting the apex and the edges where the first base surface and the two first slanted surfaces intersect, and the second cutting blade part has cutting blades formed at the edge constituting the apex and the edges where the second base surface and the two second slanted surfaces intersect. Particularly, the angle made by sandwiching the apex by the second slanted surfaces is smaller than the angle made by sandwiching the apex by the first slanted surfaces. Therefore, the increase rate of cutting blade's width from the first cutting blade part to the body part, which are both formed on either side of the second bottom surface, is smaller than the increase rate of cutting blade's width of the first cutting blade part, which are both formed on either side of the first bottom surface. That is, with the second cutting blade part, the incision gradually widens. As a result, the insertion mark may be made smaller.

Furthermore, a third cutting blade part continuing to the second cutting blade part on the body part side formed on the cutting blade component includes: two first slanted surfaces formed sandwiching the apex;

grooves comprising slanted surfaces having a pair of an upper rim and a lower rim approximately parallel to the apex and respectively formed on the two first slanted surfaces, wherein an angle made by sandwiching the apex by slanted surfaces is smaller than the angle made by sandwiching the apex by the first slanted surfaces; and third slanted surfaces formed separated from the apexes of the grooves. As a result, the cutting blades formed at the edges made by the third slanted surfaces and the third bottom surface may be sharper than the angles of the cutting blades formed at the edges of the apex. This allows secured, favorable insertion property.

With the suture needle according to the present invention, as described above, the angles of the cutting blades formed at the edges of the apex from the first cutting blade part to the third cutting blade part are fixed but the angles of the cutting blades formed at the edges of the two slanted surface and the bottom surface are different. That is, the angles of the cutting blades formed at the edges between the second slanted surfaces and the second bottom surface of the second cutting blade part are larger than the angles of the cutting blades of the first cutting blade part. Moreover, the angles of the cutting blades formed at the edges between the third slanted surfaces and the third bottom surface of the third cutting blade part are smaller than the angles of the cutting blades of the first cutting blade part. As a result, when suturing tissue, the insertion resistance is dispersed, and favorable insertion property can be secured.

DESCRIPTION OF EMBODIMENTS

Figure 1:
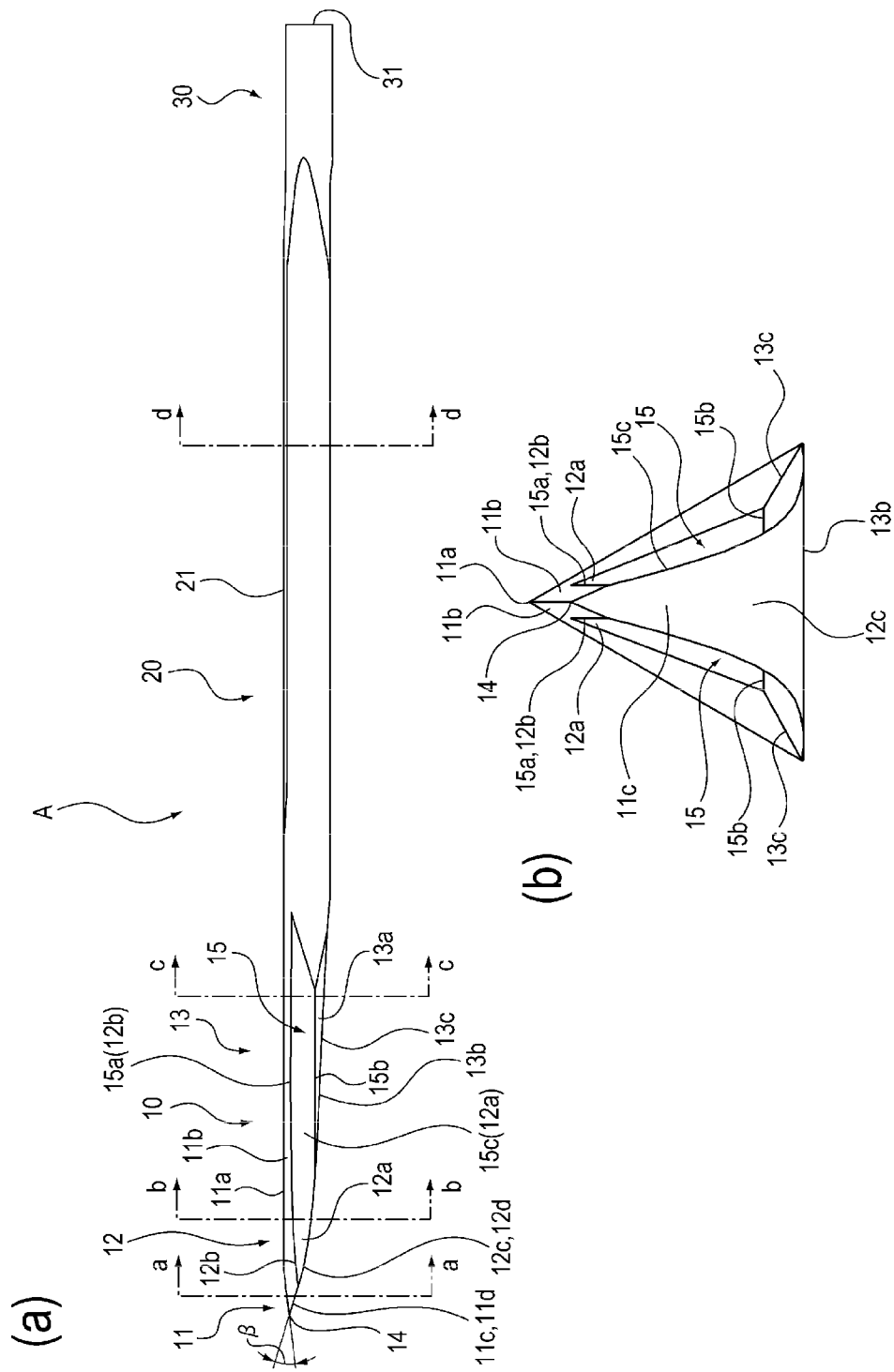
FIG. 1 shows side views for describing a structure of a medical suture needle according to an embodiment.

A suture needle according to the present invention is described below. The suture needle according to the present invention is constituted by a cylindrical rod made of stainless steel. While the material of the needle is not limited as long as it is stainless steel, it is preferable to use a fibrously extending wire rod having the thickness of the desired suture needle as the material which is formed by subjecting the cylindrical rod made of austenitic stainless steel to cold drawing processing at a predetermined area reduction rate.

The suture needle to be used according to the present invention is formed having a triangular cross-sectional shape, and includes a cutting blade component having a sharp point, and a body part continuing to the cutting blade component. A first cutting blade part, a second cutting blade part, and a third cutting blade part are formed continuously between the point of the cutting blade component and the body part. A base end part is formed on the end part side opposite the cutting blade component of the body part, and a blind hole or a pair of spring posts for attaching the suture thread to the base end part is also formed on the end part side.

The suture needle to be used according to the present invention can have any shape and is not limited to a curved needle that is curved in an arc shape, or a linear straight needle. Moreover, when the suture needle to be used is a curved needle, the apex can be either on the inner side or outer side of the curve.

The cutting blade component is formed in a so-called tapered form, gradually decreasing in degree of thickness from the body part to the point and the first cutting blade part to the third cutting blade part are formed within the tapered form. Length and degree of thickness of each of the first cutting blade part to the third cutting blade part are not limited but corresponded to the size of the suture needle to be used and set appropriately. Moreover, the cross-section of the body part may employ a triangular or square shape, but is not limited thereto.

Note that in the description below, 'degree of thickness' does not refer to the diameter of a circle connecting the vertices of the cross-sectional shape, such as triangle, square, nor the diameter of the inscribed circle of the cross-sectional shape, but refers to the diameter of a circle having an area corresponding to the area of the cross-sectional shape.

A configuration of a suture needle according to an embodiment is described below with reference to attached drawings. A suture needle A illustrated in the drawings is formed linear, and it can be used as a suture needle as it is, or the linear suture needle A can be bent in a later step and used as a curved suture needle.

The suture needle A according to the embodiment is formed by cutting to a predetermined length, a wire rod made of austenitic stainless steel that has been subjected to cold drawing processing until a predetermined diameter, subjecting an end side of the material to press working into a triangular prism, grinding the triangular prism, and subjecting the resulting triangular prism to blind hole machining.

The suture needle A has a cutting blade component 10 formed on one side, a body part 20 for a doctor to grasp using a needle holder so as to maneuver formed continuing to the cutting blade component 10, and a base end part 30 for attaching a suture thread (omitted from the drawing) formed continuing to the body part 20.

The suture needle A has the cutting blade component 10 and the body part 20 formed having a triangular cross-section. A region corresponding to the triangular apex of the cutting blade component 10 is an apex functioning as a cutting blade of a first cutting blade part 11, a second cutting blade part 12, and a third cutting blade part 13. Moreover, a region corresponding to the triangular apex of the body part 20 is a ridge 21 not functioning as a cutting blade.

The suture needle A according to the embodiment has the base end part 30 formed having a circular cross-section and a blind hole (omitted from the drawing) formed in an end surface 31. An end of the suture thread is then inserted in the blind hole and attached by caulking the part of the base end part 30 corresponding to the blind hole. However, such a structure for attaching the suture thread to the suture needle is not limited to only the embodiment, and may naturally be a structure where the base end part 30 is formed in a flat shape, a pair of spring posts is formed on the formed flat surface, and the suture thread is passed through between the posts and then attached.

The cutting blade component 10 has a function of piercing and incising tissue to be sutured. This cutting blade component 10 has a sharp point 14 formed on the front end; the first cutting blade part 11, the second cutting blade part 12, and the third cutting blade part 13 are continuously formed from the point 14 side; and the body part 20 is formed continuing from the third cutting blade 13.

Figure 3:
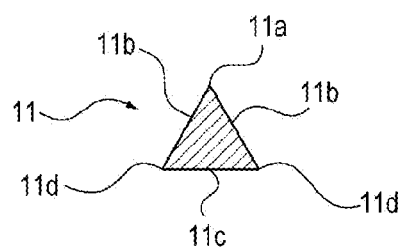
FIG. 3 shows partial cross-sections for describing the structure of the medical suture needle according to the embodiment.
Figure 3:
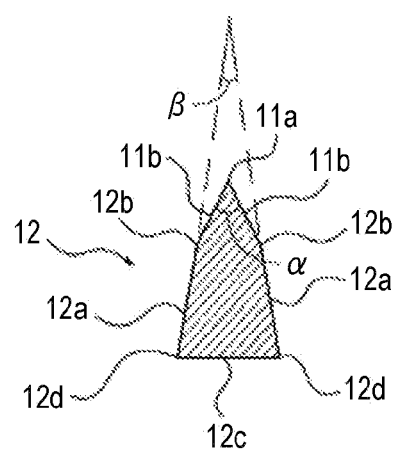
Figure 3:
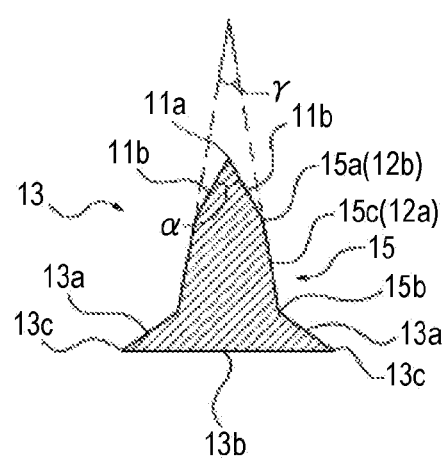
Figure 3:
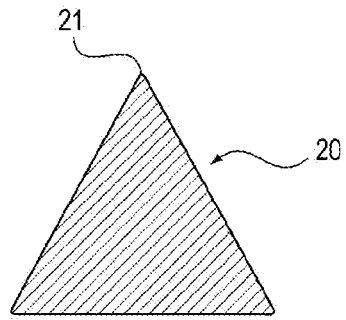

The cutting blade component 10 is formed in a tapered shape such that degree of thickness gradually decreases from the body part 20 to the point 14. That is, when viewing the suture needle A from the point 14 (see FIG. 3), the cutting blade component 10 is within the cross-section of the body part 20 without any region protruding from the side surface of the body part 20. Therefore, the insertion mark may be formed smaller.

The first cutting blade part 11 includes two first slanted surfaces 11b formed sandwiching an apex 11a, and a first bottom surface 11c sandwiched by the two first slanted surfaces 11b. Moreover, an edge formed on the apex 11a functions as a cutting blade 11a, and edges where the two first slanted surfaces 11b and the first bottom surface 11c intersect are formed as cutting blades 11d. Accordingly, the apex 11a of the first cutting blade part 11 is also used as the cutting blade 11a.

The angle formed by the two first slanted surfaces 11b sandwiching the apex 11a is not limited. However, making the blade angles of the cutting blades 11a and 11d be the same is preferred to secure well-balanced, uniform insertion property. Therefore, it is preferable to set the angle between the two first slanted surfaces 11b within an appropriate angle range including 60 degrees at the center of the range. As such, it is possible to achieve high bending strength by making the cross-sectional shape of the first cutting blade part 11 an approximate equilateral triangle.

The apex 11a of the first cutting blade part 11 is formed so as to slant slightly toward the first bottom surface 11c from the straight line continuing from the ridge 21 formed on the body part 20, and the two first slanted surfaces 11b sandwiching the apex 11a approach each other toward the point 14 and intersect. Similarly, the first bottom surface 11c also approaches the apex 11a toward the point 14 and intersects at the point 14. That is, the two first slanted surfaces 11b and the first bottom surface converge at the point 14, thereby forming a sharp point 14 as a result.

Figure 2:
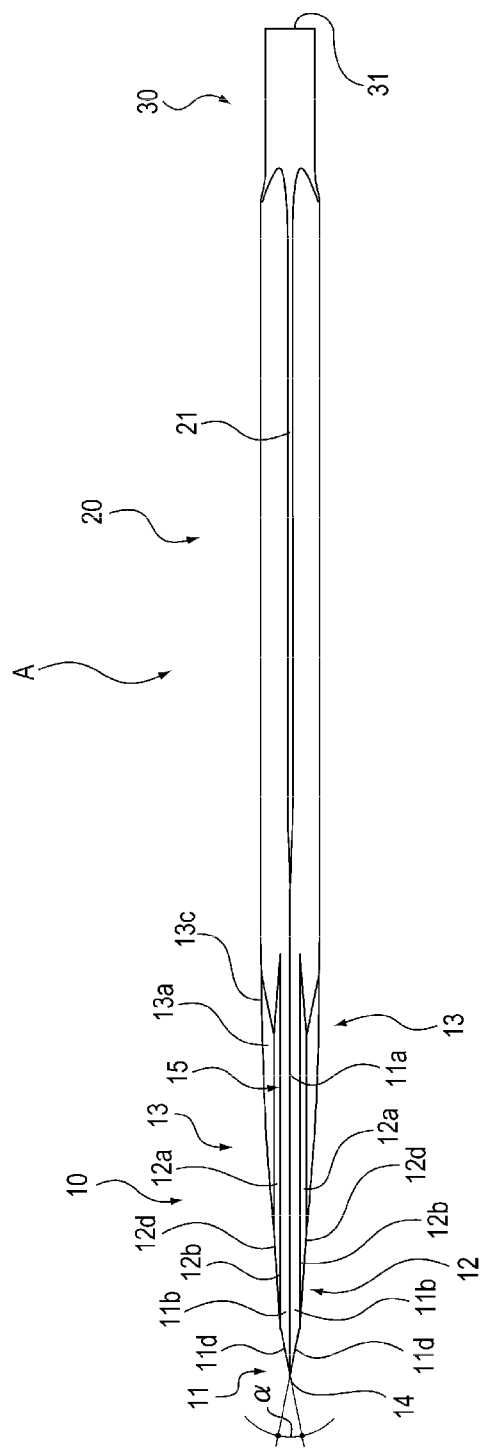
FIG. 2 is a top view for describing the structure of the medical suture needle according to the embodiment.

Based on this, since the point 14 formed on the front end portion of the first cutting blade part 11 is slightly displaced toward the center and is not on the same straight line as the ridge 21, a uniform insertion property can be secured. Angle $\alpha$ made by the two first slanted surfaces 11b at the point 14 (see FIG. 2), and angle $\beta$ made by the apex 11a and the first bottom surface 11c (see FIG. 1) are not limited, but are preferably set appropriately in accordance with the tissue to be pierced.

In the embodiment, the angles $\alpha$ and $\beta$ are set within a range of approximately 20 to 30 degrees.

Moreover, the method of processing the first slanted surfaces 11b and the first bottom surface 11c is not limited, and a method allowing each of the edges to function as a cutting blade may be employed. Such a processing method includes grinding, press working, and a combination of them, and any one of these processes may also be employed.

The apex 11a of the first cutting blade part 11 and the two first slanted surfaces 11b that are formed sandwiching the apex 11a are formed along the entire length of the cutting blade component 10 and continuing from the cutting blade component 10 to the body part 20. However, the apex 11a functions as a cutting blade of the cutting blade component 10 but does not function as a cutting blade of the body part 20.

A second cutting blade part 12 includes the two first slanted surfaces 11b that are formed sandwiching the apex 11a, second slanted surfaces 12a, each having a rim 12b and formed on the two first slanted surfaces 11b, and a second bottom surface 12c sandwiched by the second slanted surfaces 12a. An edge constituting the apex 11a functions as a cutting blade 11a, and cutting blades 12d are formed at edges where the second base surface 12c and the two second slanted surfaces 12a intersect.

The angle made by sandwiching the apex 11a by two second slanted surfaces 12a is smaller than the angle made by the first slanted surfaces 11b, and the second slanted surfaces are formed further on the bottom surface side than the apex 11a of the first slanted surfaces 11b. Therefore, the rims 12b approximately parallel to the apex 11a are formed on the first slanted surfaces 11b at positions separated from the apex 11a.

That is, the second cutting blade part 12 includes the apex 11a shared with the first cutting blade part 11, the two first slanted surfaces 11b sandwiching the apex 11a, and the second slanted surfaces 12a having sharper angles than the first slanted surfaces 11b. The cutting blades 12d are formed at the edges where the second slanted surfaces 12a and the second bottom surface 12c intersect.

Accordingly, the second cutting blade part 12 has an approximately pentagonal cross-sectional shape, and assuming that there are lines extending along the first slanted surfaces 11b and that the extending lines intersect with a line extending along the second bottom surface 12c, the interval between the cutting blades 12d is smaller than the interval between the intersecting points. Moreover, the angle between the cutting blades 12d is greater than the angle between the cutting blades 11d of the first cutting blade part 11. Furthermore, since the degree of thickness of the second cutting blade part 12 gradually increases from the first cutting blade part 11 toward the third cutting blade part 13, the interval between the cutting blades 12d also gradually increases.

As a result, change in insertion resistance occurs when shifting from the first cutting blade part 11 to the second cutting blade part 12; however, this does not impair a doctor's operability.

The third cutting blade part 13 is formed continuing to the second cutting blade part 12 on the body part 20 side. This third cutting blade part 13 shares the apex 11a and the two first slanted surfaces 11b that are formed sandwiching the apex 11a with the first cutting blade part 11 and the second cutting blade part 12.

Moreover, each of the two first slanted surfaces 11b has a groove 15, third slanted surfaces 13a are formed in each of the grooves 15 on the side separated from the apex 11a, and a third bottom surface 13b is sandwiched by the third slanted surfaces 13a. Cutting blades 13c are formed at the edges where the third bottom surface 13b and the third slanted surfaces 13a intersect.

The grooves 15 each have a pair of an upper rim 15 and a lower rim 15b approximately parallel to the apex 11a, and a slanted surface 15c where the angle made by sandwiching the apex 11a is smaller than the angle made by the first slanted surfaces 11b. That is, the grooves 15 are formed along the length from the second cutting blade part 12 to the body part 20, the first slanted surfaces 11b are formed on the apex 11a side of the grooves 15, and the third slanted surfaces 13a are formed on the bottom surface 13b side.

Accordingly, the width of the grooves 15 is smaller than the interval between the third bottom surface 13b and the apex 11a along the first slanted surfaces 11b. Moreover, while the angle made by the two slanted surfaces 15c is not limited, it is preferable that the angle is the same as the angle made by the second slanted surfaces 12a formed on the second cutting blade part 12. In particular, sharing the slanted surface 15c with the second slanted surfaces 12a is preferable.

Therefore, in the embodiment, the grooves 15 of the third cutting blade part 13 are formed in a state where the second slanted surfaces 12a of the second cutting blade part 12 are extended.

As to the third cutting blade part 13 configured as described above, the interval between the cutting blades 13c that are formed at the edges where the third slanted surfaces 13a and the third bottom surface 13b intersect may be approximately equal to the interval between the intersecting points when the extending lines of the first slanted surfaces 11b intersect with the third bottom surface 13b. Moreover, the angle between the cutting blades 13c may be smaller than the angle between the cutting blades 11d of the first cutting blade part 11.

That is, the third cutting blade part 13 has a larger interval between the cutting blades 13c than the interval between the cutting blades 12d of the second cutting blade part 12, and the angle made by the cutting blades 13c is smaller than the angle made by the cutting blades 12d. Therefore, when shifting from the second cutting blade part 12 to the third cutting blade part 13, the insertion resistance varies yet the insertion property is not impaired.

The processing method for forming the groove 15 (of the second slanted surface 12a) is not limited, and grinding or press working may be employed instead. In the case of forming the groove 15 through grinding, it is preferable to grind the first slanted surfaces 11b, which are formed sandwiching the apex 11a, from the region corresponding to the second cutting blade part 12 to the body part 20 along the length of the cutting blade component 10. In the case of forming the groove 15 through pressing, it is preferable to press the first slanted surfaces 11b, which are formed sandwiching the apex 11a, from the region corresponding to the second cutting blade part 12 to the body part 20 along the length of the cutting blade component 10.

Note that in the case of forming the first slanted surfaces 11b, the first bottom surface 11c, the second bottom surface 12c, and the third slanted surfaces 13b that constitute the cutting blade component 10, grinding is preferred for securing incisional properties of the cutting blades at the edges 11a and the cutting blades 11d, 12d, and 13c of the cutting blade parts 11 to 13, respectively, to cut tissue.

After the shape of the suture needle A is prepared through grinding or press working as described above, an electrolytic polishing process and a silicone coating process are carried out so as to manufacture the suture needle A to be used. Note that when the suture needle to be used is a curved needle, bending is carried out before the electrolytic polishing process. In particular, if silicone is applied to the suture needle A, silicone gets into the grooves 15 of the third cutting blade part 13 and thus does not peel off easily, and increase in insertion resistance can be suppressed even if inserting times are increased.

Comparative tests of cutting quality of the suture needle A according to the present invention configured as described above and a conventional suture needle having a groove formed along the length of the cutting blade part (hereafter referred to as 'conventional suture needle') are conducted. In the comparative tests, five samples of the suture needle A and the same of the conventional suture needle with the same degree of thickness D are fabricated, and the same synthetic resin sheet is pierced all the way through fifteen times with each of the samples to measure insertion resistance (N). Test 1 uses samples having a degree of thickness D of 0.33 mm. Test 2 uses samples having a degree of thickness D of 0.43 mm. Test 3 uses samples having a degree of thickness D of 0.53 mm.

Results of Test 1 for the suture needle A according to the present invention show an average of approximately 0.42N for the first insertion of the five samples, an average of approximately 0.53N for the tenth insertion, and an average of approximately 0.59N for the fifteenth insertion. In contrast, the conventional suture needles show an average of approximately 0.60N for the first insertion, an average of approximately 0.80N for the tenth insertion, and an average of approximately 0.88N for the fifteenth insertion.

Accordingly, as a result of Test 1, it can be said that the suture needle A according to the present invention has a sufficiently smaller insertion resistance than the conventional suture needle.

Results of Test 2 for the suture needle A according to the present invention show an average of approximately 0.46N for the first insertion of the five samples, an average of approximately 0.59N for the tenth insertion, and an average of approximately 0.61N for the fifteenth insertion. In contrast, the conventional suture needles show an average of approximately 0.60N for the first insertion, an average of approximately 0.75N for the tenth insertion, and an average of approximately 0.80N for the fifteenth insertion.

Accordingly, as a result of Test 2, it can be said that the suture needle A according to the present invention has a sufficiently smaller insertion resistance than the conventional suture needle.

Results of Test 3 for the suture needle A according to the present invention show an average of approximately 0.52N for the first insertion of the five samples, an average of approximately 0.69N for the tenth insertion, and an average of approximately 0.76N for the fifteenth insertion. In contrast, the conventional suture needles show an average of approximately 0.65N for the first insertion, an average of approximately 0.80N for the tenth insertion, and an average of approximately 0.86N for the fifteenth insertion.

Accordingly, as a result of Test 3, it can be said that the suture needle A according to the present invention has a sufficiently smaller insertion resistance than the conventional suture needle.

The size of insertion marks in the above insertion tests are visually evaluated, and slightly smaller marks than with the conventional suture needles are confirmed.

Comparative tests of bending strength of the suture needle A according to the present invention and the conventional suture needle are conducted. This test uses samples having a degree of thickness D of 0.43 mm. Each of the samples is secured with a vice at a position 3 mm from the point 14, so as to measure bending moment when a force is applied to the body part 20 and bent to 90 degrees. Thickness at the position 3 mm from the point 14 of the samples is approximately 0.35 mm.

This test shows that a maximum bending moment of the suture needle A according to the present invention when bending at 90 degrees is 39.12 mN·m, and that that of the conventional suture needle is 26.05 mN·m. The maximum bending moment of the suture needle A according to the present invention is sufficiently greater than that of the conventional suture needle. Accordingly, it can be said that the bending strength is large.

INDUSTRIAL APPLICABILITY

The suture needle A according to the present invention is applicable as either a straight suture needle or a curved suture needle.

EXPLANATION OF REFERENCES

A: Suture needle
10: Cutting blade component
11: First cutting blade part
11*a*: Apex
11*b*: First slanted surface
11*c*: First bottom surface
11*d*: Cutting blade
12: Second cutting blade part
12*a*: Second slanted surface
12*b*: Rim
12*c*: Second bottom surface
12*d*: Cutting blade
13: Third cutting blade part
13*a*: Third slanted surface
13*b*: Third bottom surface
13*c*: Cutting blade
14: Point
15: Groove
15*a*: Upper rim
15*b*: Lower rim
15*c*: Slanted surface
20: Body part
21: Ridge
30: Base end part
31: End surface

The invention claimed is:

1. A medical suture needle made of stainless steel, comprising:
a cutting blade component; and
a body part continuing to the cutting blade component;
the cutting blade component having a sharp point and formed with a shape whose degree of thickness decreases from the body part to the sharp point comprises: a first cutting blade part continuing from the sharp point, and a second cutting blade part continuing from the first cutting blade part; wherein,
the first cutting blade part comprises: two first slanted surfaces formed sandwiching an apex, and a first bottom surface sandwiched by the two first slanted surfaces; wherein cutting blades are formed at an edge constituting the apex and at edges where the first bottom surface and the two first slanted surfaces intersect; and
the second cutting blade part comprises: the two first slanted surfaces formed sandwiching the apex; two second slanted surfaces having rims, which are approximately parallel to the apex, formed on the two respective first slanted surfaces, or on an apex side of the second slanted surfaces, wherein an angle made by sandwiching the apex by the second slanted surfaces is smaller than an angle made by sandwiching the apex by the two first slanted surfaces; and a second bottom surface sandwiched by the two second slanted surfaces; wherein cutting blades are formed at an edge constituting the apex and at edges where the second bottom surface and the two second slanted surfaces intersect.

2. The medical suture needle of claim 1, wherein a third cutting blade part continuing to the second cutting blade part on a body part side is formed on the cutting blade component,
the third cutting blade part comprising:
the two first slanted surfaces formed sandwiching the apex;
grooves comprising slanted surfaces having a pair of an upper rim and a lower rim approximately parallel to the apex and respectively formed on the two first slanted surfaces, wherein an angle made by sandwiching the apex by the slanted surfaces is smaller than the angle made by sandwiching the apex by the two first slanted surfaces;
two third slanted surfaces formed in each of the grooves on a side separated from the apex; and
a third bottom surface sandwiched by the two third slanted surfaces, wherein cutting blades are formed at the edge constituting the apex and at edges where the third bottom surface and the two third slanted surfaces intersect.

* * * * *